United States Patent
Angel et al.

(10) Patent No.: US 6,248,786 B1
(45) Date of Patent: Jun. 19, 2001

(54) USE OF SULPHONANILIDE DERIVATIVES TO OBTAIN A MEDICINE FOR TREATING RETROGRADE EJACULATION OR ASPERMIA

(75) Inventors: Itzchak Angel, Nes-Ziyyona (IL); Denis Martin, Sainte Geneviéve des Bois; Sonia Arbilla, Paris, both of (FR)

(73) Assignee: Sanofi-Synthelabo, Paris (FR)

(*) Notice: Subject to any disclaimer, the term of this patent is extended or adjusted under 35 U.S.C. 154(b) by 0 days.

(21) Appl. No.: 09/508,222

(22) PCT Filed: Sep. 10, 1998

(86) PCT No.: PCT/FR98/01928

§ 371 Date: May 22, 2000

§ 102(e) Date: May 22, 2000

(87) PCT Pub. No.: WO99/12536

PCT Pub. Date: Mar. 19, 2000

(30) Foreign Application Priority Data

Sep. 11, 1997 (FR) .................................. 97 11284

(51) Int. Cl.$^7$ .................................. A61K 31/18
(52) U.S. Cl. ............................................. 514/605
(58) Field of Search .............................. 514/605

(56) References Cited

U.S. PATENT DOCUMENTS

| | | | |
|---|---|---|---|
| 5,610,174 | * | 3/1997 | Craig et al. .......................... 514/401 |
| 5,922,341 | * | 7/1999 | Smith et al. .......................... 424/430 |
| 5,958,884 | * | 9/1999 | Kifor et al. ............................ 514/16 |
| 6,037,346 | * | 3/2000 | Doherty et al. ...................... 514/258 |
| 6,071,882 | * | 6/2000 | Engel et al. ........................... 514/15 |
| 6,071,915 | * | 6/2000 | Joliffe et al. ......................... 514/252 |

FOREIGN PATENT DOCUMENTS

| 538469 | 6/1991 | (EP) . |
|---|---|---|
| WO 97/06136 | 2/1997 | (WO) . |

OTHER PUBLICATIONS

Muramatsu et al, *Naunyn–Schmied. Arch. Pharmacol.*, vol. 351, No. 1, pp. 2–9, Jan. 1995.
Van Der Graaf et al., *Eur. J. Pharmacol.*, vol. 327, No. 1, pp. 25–32, May 26, 1997.
Schreiter, *Zentralblatt Fur Chirurgie*, vol. 99, No. 2, pp. 33–40, 1974.
Deplanne et al. *J. Pharmacol. Exp. Ther.*, vol. 278, No. 2, pp. 527–534, Aug. 1996.
Derwent Patent Abstract No. 199715.

* cited by examiner

*Primary Examiner*—James H. Reamer
(74) *Attorney, Agent, or Firm*—Michael D. Alexander

(57) ABSTRACT

Descriptive summary: use of a compound with the formula (I)

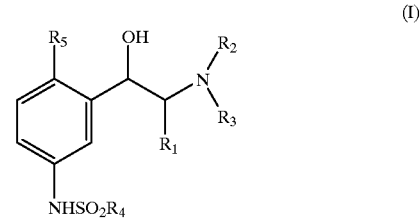

where

R1 is a hydrogen atom, a $C_{1-2}$ alkyl group, a $C_{1-2}$ fluoroalkyl group or a $C_{1-2}$ perfluoroalkyl group and $R_2$, $R_3$ and $R_4$, which may be the same or different, all represent a hydrogen atom, a straight- or branched-chain $C_{1-4}$ alkyl group or a $C_{3-4}$ cycloalkyl group, and $R_5$ is a hydrogen atom, a halogen such as fluorine or chlorine, a $C_{1-4}$ alkyl group or a straight- or branched-chain $C_{1-4}$ alkoxy group to manufacture a medicinal agent which can be used to treat ejaculation problems such as retrograde ejaculation or aspermia.

16 Claims, No Drawings

USE OF SULPHONANILIDE DERIVATIVES TO OBTAIN A MEDICINE FOR TREATING RETROGRADE EJACULATION OR ASPERMIA

This application is a 371 of PCT/FR98/01928 Sep. 10, 1998.

The object of the present invention is the use of sulfonanilide derivatives to produce a medicinal product intended for the treatment of retrograde ejaculation or aspermia.

The compounds have the following general formula (I)

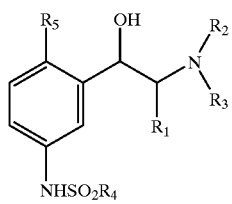

(I)

where

R1 is a hydrogen atom, a $C_{1-2}$ alkyl group, a $C_{1-2}$ fluoroalkyl group or a $C_{1-2}$ perfluoroalkyl group, and $R_2$, $R_3$ and $R_4$, which may be the same or different, all represent a hydrogen atom, a straight- or branched-chain $C_{1-4}$ alkyl group or a $C_{3-4}$ cycloalkyl group, preferably a hydrogen or a methyl and $R_5$ is a hydrogen atom, a halogen such as fluorine or chlorine, a $C_{1-4}$ alkyl group or a straight- or branched-chain $C_{1-4}$ alkoxy group, preferably a methoxy or a halogen and more particularly a fluorine.

The compounds with the general formula (I) may include one or several asymmetric carbons. They can therefore exist in the form of enantiomers or diastereoisomers. These enantiomers, diastereoisomers and mixtures of them, including racemic mixtures, form part of the invention.

The compounds with the general formula (I) may take the form of the free base or addition salts with pharmaceutically acceptable acids, which are also part of the invention.

The compounds with the general formula (I) can be prepared according to the procedures described in European Patent EP 538469 or analog procedures known to specialists.

The table which follows illustrates, by way of example, the structure of some compounds which can be used according to the invention, without however limiting the invention to these compounds.

TABLE (I)

| Number | $R_1$ | $R_2$ | $R_3$ | $R_4$ | $R_5$ | base/salt | MPt(° C) |
|---|---|---|---|---|---|---|---|
| 1(−) | H | H | H | $CH_3$ | F | HCl | 185 |
| 2(+) | H | H | H | $CH_3$ | F | HCl | 203–220 |
| 3 | H | H | H | $CH_3$ | $OCH_3$ | $CH_3SO_3H$ | 180–182 |

(−) indicates an l-enantiomer and (+) indicates a d-enantiomer

The compounds of the invention have been submitted to biological tests intended to demonstrate their contractile activity on the smooth muscles of the fornix and the arteries.

The in-vitro activity of the compounds of the invention has been investigated on the smooth muscles of the fornix and the arteries. These tests were carried out on New-Zealand rabbits weighing between 3 and 3.5 kg. The animals were killed by cervical dislocation and then rings were prepared from the tissue of the mesenteric arteries and strips from the fornix. The rings or strips of tissue were immersed in modified Krebs' solution which was oxygenated with a mixture containing 95% $O_2$ and 5% $CO_2$. Each tissue sample was subjected to a tension of 1 g and then cumulative doses of phenylephrine were added and the concentration/response curve plotted. After rinsing the tissue, the test compound was added at cumulative doses and the concentration/response curve plotted. The contractile effect of each compound was assessed by calculating the value of $pD_2$ (the negative logarithm of the concentration of the agonist which induces 50% of the maximum contraction) and the maximum effect, expressed as a percentage of the contraction obtained with phenylephrine (% Emax).

The results obtained show that the compounds corresponding to the invention, display:

a pD2 of the fornix, which is usually between 4 and 6 a pD2 of the artery which is usually less than 5 a % Emax phenylephrine for the fornix which is greater than 30% and usually between 40 and 90% a % Emax for the artery which is usually greater than 30%

All the above data show that the compounds according to the invention have a strong contractile effect on the smooth muscles of the fornix and a weak contractile effect on the artery.

They can be used for medicinal purposes, particularly as an agent to contract the smooth muscles of the fornix, and more particularly still, to treat ejaculation problems such as retrograde ejaculation or aspermia. In this indication, the compounds according to the invention demonstrate good efficacy and usually, less side effects than the drugs conventionally used for such treatment, notably with regard to side effects involving the cardiovascular system.

The compounds according to the invention can be formulated in various appropriate pharmaceutical forms for administration by the digestive or parenteral routes as required and combined with at least one pharmaceutical excipient. The appropriate pharmaceutical forms consist, for example, of tablets, capsules, sugar-coated tablets, solutions for oral use or for injection, syrups and suppositories.

These pharmaceutical forms can contain sufficient quantities to permit a daily dose of 1 μg/kg to 30 mg/kg.

What is claimed is:

1. A method to contract the smooth muscles of the fornix which comprises administering to a patient in need of such treatment an effective amount of a compound with the formula (I)

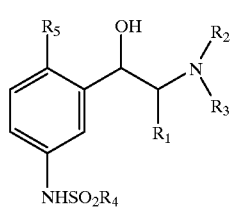

(I)

where $R_1$ is a hydrogen atom, a $C_{1-2}$ alkyl group, a $C_{1-2}$ fluoroalkyl group or a $C_{1-2}$ perfluoroalkyl group and $R_2$, $R_3$ and $R_4$, which may be the same or different, all represent a hydrogen atom, a straight- or branched-chain $C_{1-4}$ alkyl group or a $C_{3-4}$ cycloalkyl group, and $R_5$ is a hydrogen atom, a halogen, a $C_{1-4}$ alkyl group or a straight- or branched-chain $C_{1-4}$ alkoxy group in the form of an enantiomer, diastereoisomer or a mixture of these forms, including a racemic mixture, as well as the addition salts with pharmaceutically acceptable acids.

2. A method according to claim 1 for the treatment of ejaculation problems.

3. A method according to claim 2 for the treatment of retrograde ejaculation.

4. A method according to claim 2 for the treatment of aspermia.

5. A method according to claim 1 wherein $R_1$ is hydrogen or methyl; and $R_2$, $R_3$ and $R_4$, which may be the same or different, are hydrogen or methyl.

6. A method according to claim 5 wherein $R_5$ is methoxy or halogen.

7. A method according to claim 6 wherein $R_5$ is methoxy, fluorine or chlorine.

8. A method according to claim 7 wherein $R_5$ is methoxy or fluorine.

9. A method according to claim 8 wherein $R_1$, $R_2$, and $R_3$ are hydrogen and $R_4$ is methyl.

10. A method according to claim 9 wherein $R_1$, $R_2$, and $R_3$ are hydrogen, $R_4$ is methyl and $R_5$ is fluorine.

11. A method according to claim 9 wherein $R_1$, $R_2$, and $R_3$ are hydrogen, $R_4$ is methyl and $R_5$ is methoxy.

12. A method according to claim 10 wherein the compound is in the form of the l-enantiomer.

13. A method according to claim 10 wherein the compound is in the form of the d-enantiomer.

14. A method according to claim 12 wherein the compound is in the form of a hydrochloride salt.

15. A method according to claim 13 wherein the compound is in the form of a hydrochloride salt.

16. A method according to claim 11 wherein the compound is in the form of a methanesulfonic acid salt.

* * * * *